(12) United States Patent
Buzot

(10) Patent No.: US 6,423,025 B1
(45) Date of Patent: Jul. 23, 2002

(54) CATAMENIAL APPLICATOR HAVING A FINGERGRIP

(76) Inventor: Herve Buzot, 999 Hidden Lake Dr., No. Brunswick, NJ (US) 08902

(*) Notice: Subject to any disclaimer, the term of this patent is extended or adjusted under 35 U.S.C. 154(b) by 0 days.

(21) Appl. No.: 09/608,407

(22) Filed: Jun. 30, 2000

(51) Int. Cl.$^7$ ................................................ A61F 13/20
(52) U.S. Cl. ............................................................ 604/15
(58) Field of Search ...................... 604/11–18, 285–288, 604/311, 57–60

(56) References Cited

U.S. PATENT DOCUMENTS

| | | | |
|---|---|---|---|
| 3,015,332 A | 1/1962 | Brecht | |
| 3,148,680 A | 9/1964 | Roberts et al. | |
| 3,347,234 A | 10/1967 | Voss | |
| 3,433,225 A | 3/1969 | Voss et al. | |
| 3,572,339 A | 3/1971 | Voss et al. | |
| 3,575,169 A | 4/1971 | Voss et al. | |
| 3,581,744 A | * 6/1971 | Voss ............................ | 604/15 |
| 4,048,998 A | 9/1977 | Nigro | |
| 4,412,833 A | 11/1983 | Wiegner et al. | |
| 4,447,222 A | 5/1984 | Sartinoranont | |
| 4,508,531 A | 4/1985 | Whitehead | |
| 4,536,178 A | 8/1985 | Liehstein et al. | |
| 4,573,963 A | 3/1986 | Sheldon | |
| 4,573,964 A | 3/1986 | Huffman | |
| 4,620,534 A | 11/1986 | Zartman | |
| 4,718,898 A | 1/1988 | Puletti et al. | |
| 4,755,164 A | 7/1988 | Hinzmann | |
| 4,857,393 A | 8/1989 | Kato et al. | |
| 4,921,474 A | 5/1990 | Suzuki et al. | |
| 4,923,440 A | 5/1990 | Genaro | |
| 5,041,080 A | 8/1991 | Shimatani et al. | |
| 5,135,475 A | 8/1992 | Nakanishi et al. | |
| 5,330,421 A | 7/1994 | Tarr et al. | |
| 5,346,468 A | 9/1994 | Campion et al. | |
| 5,453,085 A | 9/1995 | Schoelling | |
| 5,554,108 A | 9/1996 | Browning et al. | |
| 5,599,293 A | 2/1997 | Orenga et al. | |
| 5,614,230 A | 3/1997 | Weyenberg et al. | |
| 5,702,553 A | 12/1997 | Iskra et al. | |
| 5,709,652 A | 1/1998 | Hagerty | |
| 5,788,663 A | 8/1998 | Igaue et al. | |
| 5,891,123 A | 4/1999 | Balzar | |
| 5,910,520 A | 6/1999 | Dabi et al. | |

FOREIGN PATENT DOCUMENTS

| | | |
|---|---|---|
| EP | 0481484 B1 | 4/1992 |
| FR | 2374022 | 7/1978 |
| GB | 1108291 | 4/1968 |
| GB | 1272863 | 5/1972 |
| GB | 1272864 | 5/1972 |
| GB | 2166656 A | 5/1986 |
| GB | 2132484 | 7/1986 |
| WO | WO98/44885 | 10/1998 |
| WO | 0100125 | 1/2001 |

OTHER PUBLICATIONS

U.S. patent application Ser. No. 09/602,950 (PPC–732).
PCT International Search Report, Feb. 12, 2002, PCT/US01/20513.

* cited by examiner

Primary Examiner—Dennis Ruhl

(57) ABSTRACT

The present invention relates to applicators for inserting objects into body cavities, and to methods for making the same. The applicators are particularly useful for inserting catamenial and prophylactic devices into a vaginal canal. The applicators comprise a tubular insertion member and a retrofitted gripping member. The gripping member comprises a gripping sheet which superposes upon itself about the insertion member multiple times and provides resistance to movement of a user's manual digit in response to longitudinal forces on the tubular insertion member.

33 Claims, 4 Drawing Sheets

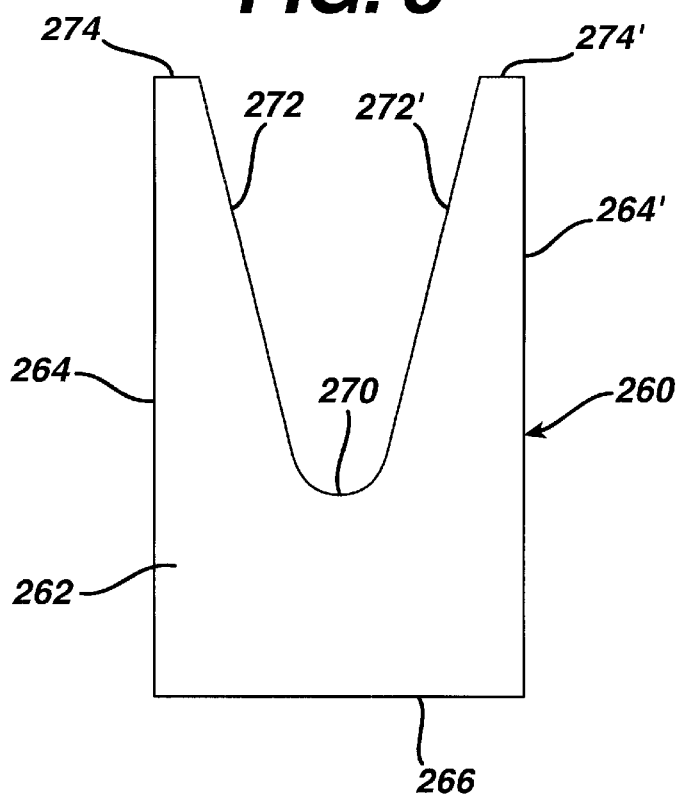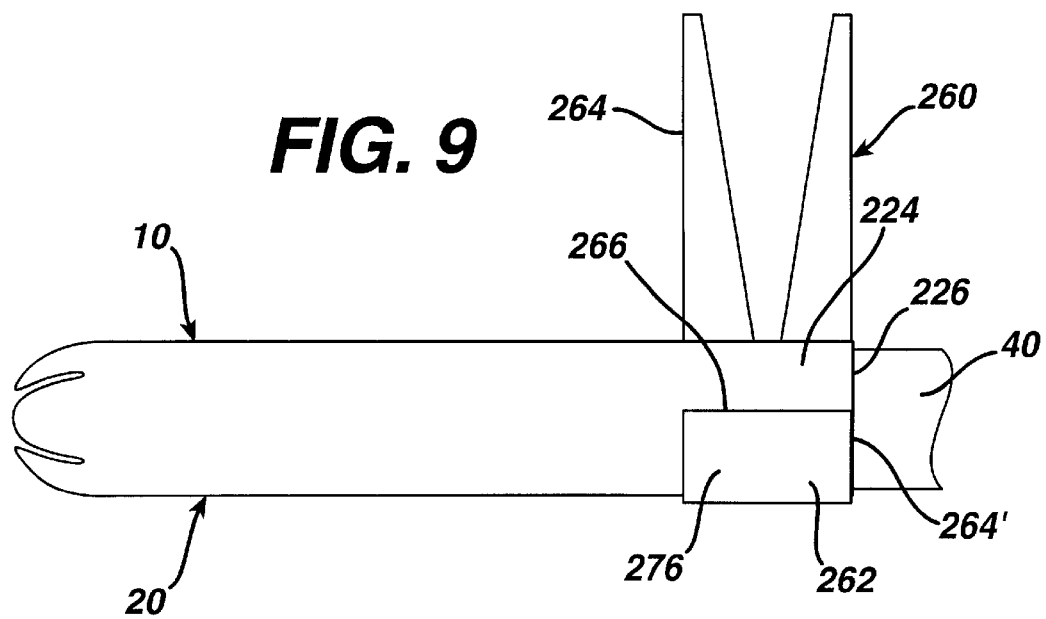

CATAMENIAL APPLICATOR HAVING A FINGERGRIP

CROSS-REFERENCE TO RELATED APPLICATIONS

This application is related to the following copending application: U.S. Ser. No. 09/602,950, filed on Jun. 23, 2000, entitled "Applicator for Catamenial Device Having Improved Gripper End"

FIELD OF THE INVENTION

The present invention provides an applicator and a method of making the applicator for inserting catamenial devices into the body. In particular, the invention provides an applicator having a fingergrip that enables the user to securely grasp the applicator during use.

BACKGROUND OF THE INVENTION

Applicators for inserting and expelling objects into a body cavity typically comprise an insertion member having an insertion end and a trailing end opposite thereof, and an expulsion member slideably fitted within the insertion member. The trailing end will generally incorporate gripping features to provide a surface that allows the user to securely hold the applicator during use.

One approach to improve handling of an applicator during use is to incorporate a gripping element into or onto the surface of the insertion member at the trailing end. This allows the diameter of the insertion member to remain uniform throughout its length (i.e., diameter of the trailing end is basically be the same diameter as the insertion end). Resistance to finger slippage may be provided by incorporating apertures, projections, ribs or ridges into the trailing end of the insertion member; by scoring the trailing end; or by incorporating a roughening agent into the finish of the gripping area of the trailing end. Voss (U.S. Pat. No. 3,347,234) and Sartinoranont (U.S. Pat. No. 4,447,222) disclose the use of a ring on the trailing end, Brecht (U.S. Pat. No. 3,015,332) discloses the use of a roughened surface. Voss (U.S. Pat. No. 3,575,169) discloses elements attached to the trailing surface. Jackson (WO 98/44885) discloses an applicator barrel provided with texture by a plurality of outwardly extending deformations.

Roberts et al. (U.S. Pat. No. 3,148,680) discloses roughening the surface with a plurality of ribs. Wiegner et al. (U.S. Pat. No. 4,412,833), Orenga et al. (U.S. Pat. No. 5,599,293) and Beastall et al. (GB 2132484) disclose the scoring of the gripping portion of the outer sleeve. Weyenberg et al. (U.S. Pat. No. 5,614,230) and Iskra (U.S. Pat. No. 5,702,553) both disclose an outwardly extending curl on the trailing end of the insertion member.

Hagerty (U.S. Pat. No. 5,709,652) discloses an applicator having a plurality of finger-accepting apertures in the trailing end. The apertures provide relatively abrupt, finger accepting edges to frictionally resist movement of a user's finger.

A second approach is to significantly reduce the diameter of the applicator in the vicinity of the tubular insertion member trailing end, as can be seen in Whitehead (U.S. Pat. No. 4,508,531) and Huffman (U.S. Pat. No. 4,573,964). Schoelling (U.S. Pat. No. 5,453,085) inserts a hollow grip piece having a reduced diameter into the trailing end of the insertion member.

Lichstein et al. (U.S. Pat. No. 4,536,178) discloses a tampon applicator having a tubular barrel to house the tampon and to accommodate a slideable plunger. The rear portion of the barrel has opposing, flattened gripping surfaces with ribs. Dohzono et al. (GB 2166656A) discloses a grip portion disposed to the rear of the insertion member. The grip portion has recessed or flat, plane-like portions.

Lastly, attempts have been made to incorporate two or more physical restraints as a means for the user to hold the applicator securely during all of the steps of use. U.S. Pat. No. 4,921,474 discloses a sanitary tampon applicator comprising a plastic outer sleeve having a diameter-reduced section along a length adjacent its rear end so as to form an annular shoulder, and an annular rib at its rear open end.

While the prior art is replete with examples of fingergrips, there still remains a need for an effective fingergrip which can be retrofitted or applied to the trailing end of an applicator of any shape, comprising features that aid in insertion of catamenial devices into the body cavity.

SUMMARY OF THE INVENTION

The present invention relates to a gripping member for providing a raised area of resistance to movement of a user's manual digit. The fingergrip member member has a leading end, a trailing end, and an intermediate portion therebetween. It includes a gripping sheet having an attachment end, an outer end opposite thereof. The gripping sheet is wound up to be superposed with the outer end exposed on the outer surface of the gripping member, and the gripping member has a raised area.

The invention also relates to an applicator for delivering an object into a body cavity. The applicator has an insertion end, and a trailing end opposite the insertion end. The trailing end has an edge. The applicator has a finger gripping member as described above attached to the outer surface of the trailing end of the applicator.

An applicator according to this invention can be formed by a method including the step of encircling a gripping sheet about the trailing end of a tubular insertion member in a manner that the gripping sheet superposes onto itself about the tubular insertion member to form a gripping member having a leading end, a trailing end, and an intermediate portion. The trailing end of the gripping member is disposed toward the trailing end edge of the tubular insertion member.

BRIEF DESCRIPTION OF THE DRAWING

FIG. 8 is a plan view of a gripping sheet according to a first, preferred embodiment;

FIG. 9 is a side elevation of the sheet from FIG. 1 attached to a tampon insertion member (plunger shown broken away)

DETAILED DESCRIPTION OF THE INVENTION

Figure 1:
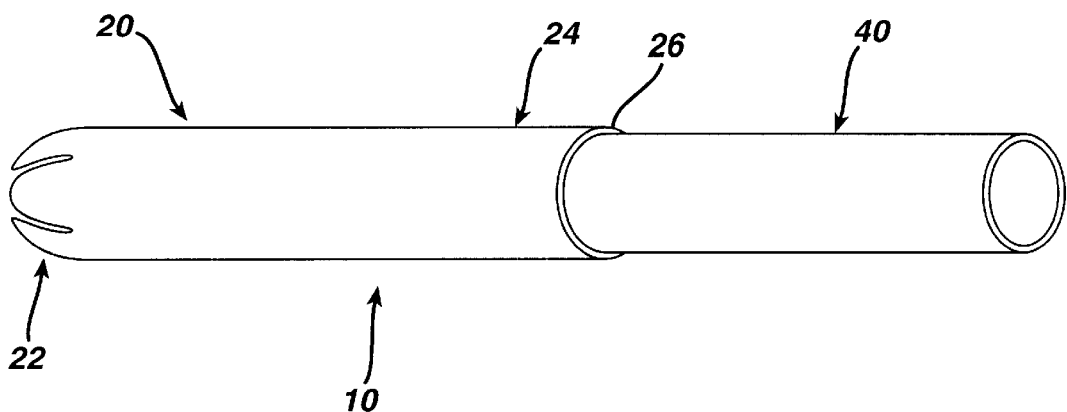
FIG. 1 is a perspective view of tampon applicator.

Referring now to the drawings, there are in the various figures multiple embodiments of fingergrips that are particularly useful for aiding in the insertion of catamenial and prophylactic devices into a vaginal canal.

FIG. 1 illustrates a generic applicator 10 comprising two tubular elements: insertion member 20 and plunger 40. Insertion member 20 has insertion end 22 and trailing end 24. Trailing end 24 has edge 26. Plunger 40 is slideably fitted within the trailing end 24.

Referring to FIGS. 2–10, the applicator 10 of the present invention further comprises a gripping member that can be manufactured separately from the insertion and plunger members and thereafter immovably affixed to at least a portion of trailing end 24 of insertion member 20, or it can be formed about the trailing end 24 of insertion member 20.

Figure 2:
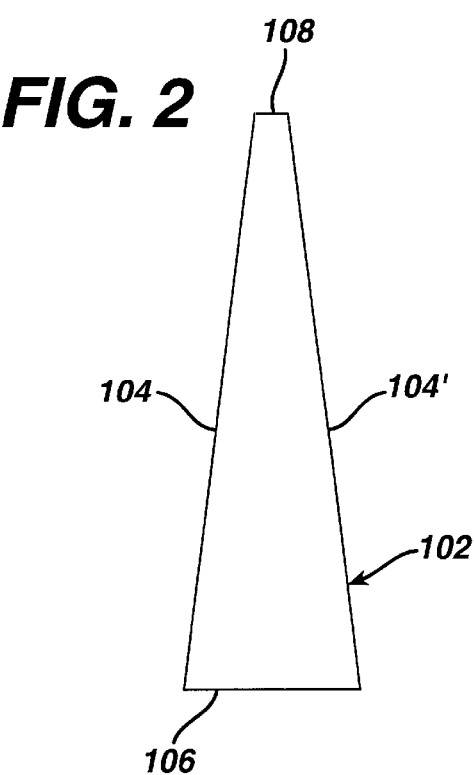
FIG. 2 is a plan view of a gripping sheet according to a second, preferred embodiment.
Figure 3:
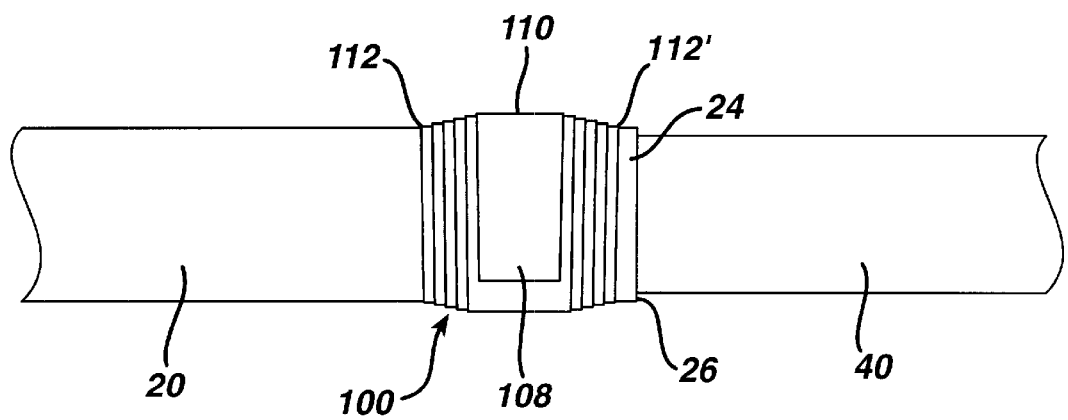
FIG. 3 is a side elevation of a tampon applicator having a finger grip according to a second, preferred embodiment (plunger shown broken away)

Another preferred embodiment of the present invention is shown in FIGS. 2 and 3. As seen in FIG. 2, sheet 102 has two longitudinal sides 104, 104', attachment end 106 and outer end 108. Although not necessary, longitudinal sides 104, 104' may be symmetrical. Attachment end 106 may be affixed perpendicularly to trailing end 24 of insertion member 20 (not shown). While outer end 108 is shown as blunt, the end may be of any configuration. Especially preferred are ends that are blunt or angled or have sharp or rounded points. The gripping member 100 is formed by superposing sheet 102 completely around insertion member 20 with the outer end 108 exposed as shown in FIG. 3. The central portion 110 of gripping member 100 has an increased height compared to leading and trailing gripper ends 112, 112'.

Figure 4:
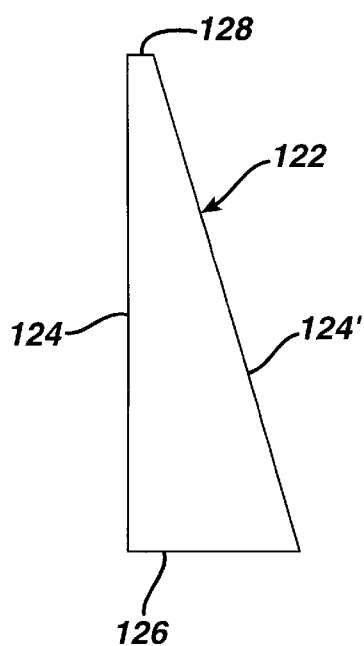
FIG. 4 is a plan view of a gripping sheet according to a third embodiment.
Figure 6:
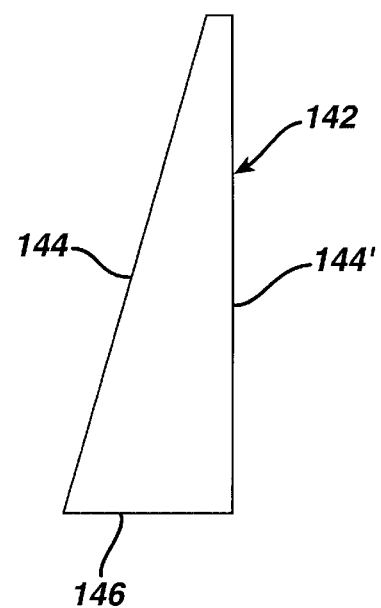
FIGS. 6 and 7 show an alternate example of the third embodiment.
Figure 5:
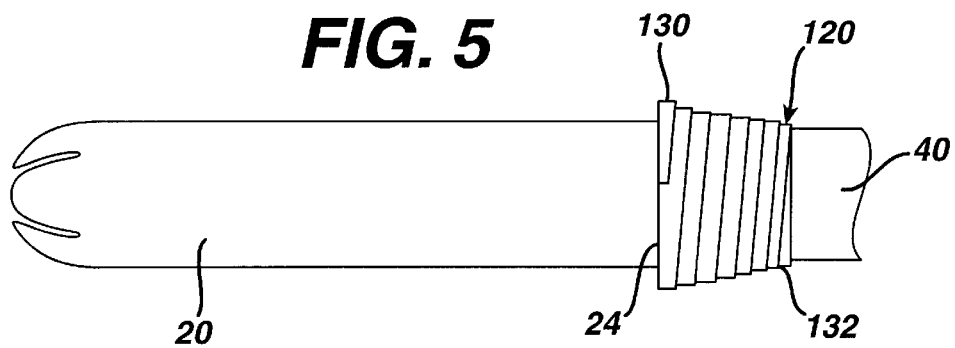
FIG. 5 is a side elevation of a tampon applicator having a finger grip according to a third embodiment (plunger shown broken away)

FIGS. 4–7 show gripping sheet 122 comprising attachment end 126, two longitudinal sides 124, 124' and outer end 128. One of the longitudinal sides, either 124 or 124', forms a right angle with attachment end 126. For instance, as illustrated in FIG. 4, longitudinal side 124 forms a right angle with attachment end 126. When gripping sheet 122 is attached to trailing end 24 and wrapped around insertion member 20, gripping member 120 is formed. As shown in FIG. 5, leading gripper end 130 comprises a thicker or more built up gripping area than trailing gripper end 132. Similarly, as seen in FIG. 6, longitudinal side 144' forms a right angle with attachment end 146. After wrapping sheet 142 about trailing end 24 to form gripping member 140, trailing gripper end 150 comprises a thicker gripping area than leading gripper end 152. In FIGS. 4 and 6, the longitudinal sides (sides 124, 124' in FIG. 4 and 144, 144' in FIG. 6) are unequal in length.

The gripping member may be formed from multiple gripping sheets. For example, two trapezoidal or triangular shaped gripping sheets (such as those seen in FIGS. 2, 4 and 6) can be positioned adjacent each other, either touching or slightly separated, on the trailing end of the insertion member. The resultant gripping member will have two thicker gripping areas and a portion of decreased diameter therebetween. Any number or placement of gripping sheets may be used.

Figure 10:
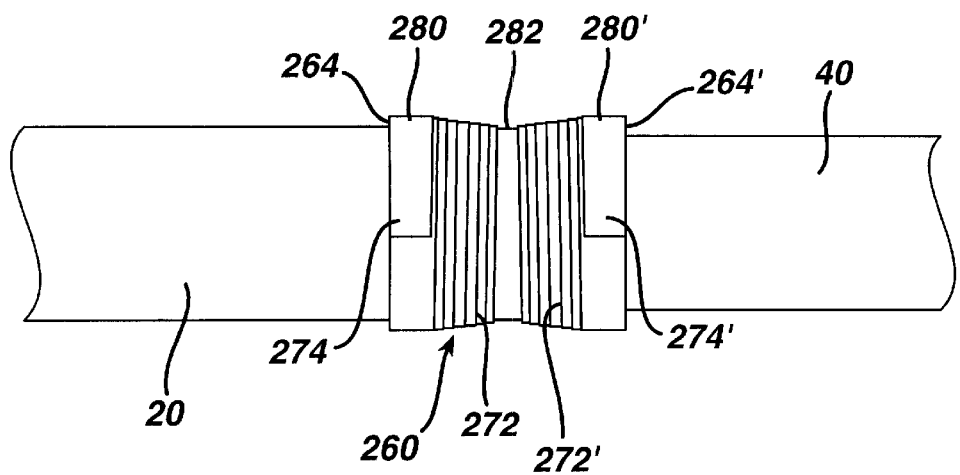
FIG. 10 is a side elevation of a tampon applicator having a finger grip according to a first, preferred embodiment (plunger shown broken away).

FIGS. 8–10 shows, in general, another preferred shape for gripping member 260. Gripping member 260 comprises sheet 262 which has two longitudinal sides 264, 264', attachment end 266, intermediate portion 270 having sides 272, 272', and outer ends 274, 274' (outer surface 276 of sheet 262 shown FIG. 9). While FIG. 8 shows the preferred embodiment for the gripping sheet having in general, an "M" shape, other shapes including "U", "↑", "V", "W", etc., (including the boxed form of the letters), are possible.

Although not necessary, sides 272, 272' may be symmetrical. As with the first embodiment, outer ends 274, 274' may be of any configuration.

FIG. 9 shows attachment of sheet 262 to trailing end 224 of insertion member 220. As shown, attachment end 266 of sheet 262 attaches perpendicular to edge 226 and encircles trailing end 224. In the preferred embodiment, longitudinal side 264' is perpendicular to the longitudinal axis and is adjacent edge 226 of the tubular insertion member. It is not necessary that longitudinal side 264' is flush with edge 226. Sheet 262 is continuously wrapped around trailing end until outer ends 274, 274' are affixed to outer side 276. Outer ends 274, 274' may form a smooth junction with outer side 276, but this is not necessary.

FIG. 10 shows a wrapped fingergrip made from sheet 262 which has been wrapped around trailing end 224 multiple times. As shown, fingergrip has leading and trailing portions 280, 280', respectively having an increased height or thickness compared to intermediate portion 282. This difference in thickness allows the user's finger to grip intermediate portion 282 and manipulate the tampon without slipping. Sides 272, 272' also form an area of resistance which aids in the user securely handling the tampon applicator during use. The multiple steps formed by sides 272, 272' provide increased surface area and resistance for the user's fingers. The thicker the material used to form gripping sheet 262, the more pronounced the steps formed by sides 272, 272' and generally, the greater frictional resistance the gripping member will exhibit to the user's fingers. A gripping sheet made from a thicker material will also cause outer ends 274, 274' to form abrupt junctions with the layers upon which outer ends 274, 274' have been overlaid.

Figure 7:
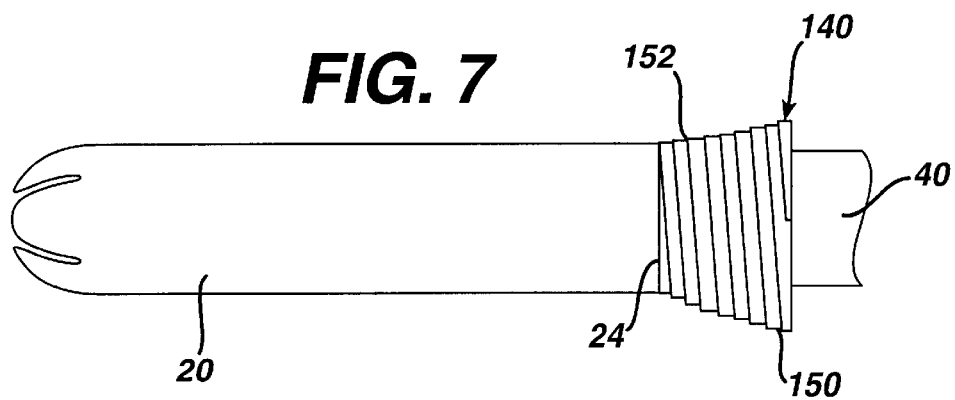

As can be seen from the embodiments described above, the gripping member profile results from the orientation of one or both longitudinal sides to the direction of winding. For example, with a tubular insertion member having a substantially uniform cross-section in the region of the gripping member, a longitudinal side edge oriented perpendicular to the longitudinal axis of the tubular insertion member will provide a thicker gripping area adjacent that longitudinal axis as shown in FIGS. 5 and 7. In other words, if the gripping sheet is wound about the tubular insertion member with a longitudinal edge aligned with itself in lower layers, that edge of the gripping member will be thicker than edges at which the longitudinal edge of overlapping layers is offset from its position in lower layers. With the same limitations, if no longitudinal side edge is oriented perpendicular to the longitudinal axis (or aligned with its position in lower layers), the thicker gripping area will be away from the side edges as shown in FIG. 3.

The longitudinal sides of the gripping sheet or of an individual gripping sheet portion are preferably not parallel to each other. This provides for the change in thickness as the sheet is superposed as it is wound onto itself, and it provides a maximum width of the gripping sheet or gripping sheet portion along the length of the gripping sheet or portion. The gripping sheets and gripping sheet portions disclosed above, generally have a maximum width at a distance from the outer end. Preferably, the maximum width is proximate the attachment end, but it could also be located intermediate the attachment and outer ends. ordinarily skilled practitioners will also recognize that the maximum width could be proximate the outer end to provide a smoother outer surface of the gripping member. However, this arrangement of relatively non-elastic materials, such as paper, could easily result in a wrinkled and unsightly outer surface of the gripping member. Of course, an elastic material would likely provide a substantially smooth outer surface.

Preferably, the longitudinal sides have a relatively smooth, straight edge. However, the finger engaging properties of the gripping member may be enhanced by providing a longitudinal side edge with a different edge treatment. A representative, non-limiting list of possible edge treatments including scallops, zigzag, notched or saw-toothed, and the like. This form edge treatment can provide a rougher leading and trailing end or other finger engaging surface of the gripping member.

Applicators are generally constructed of one of two basic materials: plastic and paperboard. Similarly, the gripping sheet can be constructed of identical materials. Paperboard products appeal to both the manufacturer and the consumer, derived from factors such as ease of manufacture, cost of manufacture, purchase cost, environmental benefits, and flushability convenience. A gripping member, manufactured separately, can be retrofitted onto a paperboard tubular insertion member, without significantly eliminating any of the noted appeal.

The cardboard used in tampon applicators can be a single layer of cardboard material, or it can be a plurality of laminated layers to provide multiple benefits relating to the various layers. Useful cardboard stock for the formation of the tubular elements includes, without limitation, paperboard, cardboard, cup stock, paper, and the like. The laminated cardboard material may include a surface layer or coating of plastic, wax, silicone, and the like that may be useful to increase the comfort to the user during insertion and withdrawal. The plastic coating may include, without limitation, polyolefins such as polyethylene and polypropylene, polyesters such as polyethylene terephthalate, polycaprolactone, polyvinyl alcohol, ethylene-vinyl acetate copolymers, cellophane, and the like. Preferred tubular element materials include laminated cardboards. Preferred laminated cardboards include plastic laminated or plastic coated cardboard materials. These plastic laminated cardboard materials may include additional layers such as adhesive layers, tie layers, and the like.

Examples of processes used for making paperboard applicator components include, without limitation: spiral winding as disclosed in U.S. Pat. No. 5,346,468; convolute winding as disclosed in U.S. Pat. No. 4,508,531; and forming a sheet around a mandrel and then sealing an overlapped seam as disclosed in U.S. Pat. Nos. 4,755,164 and 5,599,293.

Applicators may also be manufactured from conventional plastic, such as injection-moldable or blow-moldable plastic, biodegradable plastic, such as those disclosed Dabi et al. US Pat. No. 5,910,520, the entire contents herewith incorporated by reference. Generally, commercially available products are made from an olefinic-based polymer, such as polyethylene, and at least the insertion members are formed through an injection molding process. This process is used because the manufacture must balance some key characteristics of the tubular insertion member. Molding inserts and cores are machined to form a slightly tapered product, such that the wall thickness in the gripping region is relatively thick to maintain structural stability during the insertion and expulsion steps of use, while the thickness in the insertion end is minimized to provide flexibility and low expulsion force. Injection molding also enables the manufacture to make uniquely shaped tubular insertion members. There are less sophisticated/ expensive polymer forming techniques, such as extrusion and blow molding that can be employed. Manufacturing a gripping member separately, and then retrofitting it to the insertion member, allows these alternatives to be used.

The gripping member of the present invention can be made from any process that allows the gripping sheet to be formed in the desired shape and wrapped around the formed applicator. Especially preferred are gripping sheets made from woven or nonwoven materials, paper, paper products, thermoplastic, laminated plastic and polymeric sheets. Materials that are treatable in order to become pliable and manipulated can also be used. An example of such a material is a plastic sheet that becomes soft and pliable upon heating. The surface of the gripping sheets may include roughening agents including pulverized stone or sand, edge deformations, apertures, scoring, plurality of ribs or raised portions. The attachment portion of the gripping sheet is attached to the trailing end of the insertion member of the applicator.

Preferably, the gripping sheet is wrapped around the insertion member multiple times. Gripping sheets made from thin material may result in a thinner gripping member while gripping sheets made from thicker materials will likely produce relatively thick gripping members. In a particular instance, a thicker gripping member may be required if the outer surface of the gripping sheet is smooth; the edges formed by the longitudinal edges may offer a rougher gripping area for the user's finger. Dimensions for the gripping sheet may vary according to the diameter of the tubular element. Additionally, the material used for the gripping sheet may dictate the number of times the gripping sheet over-wraps the tubular element and therefore, the length of the gripping sheet may vary. Materials having a thickness ranging from about 0.05 mm to about 3 mm are preferred. Especially preferred are gripping sheets having a thickness of 0.1 mm to about 2 mm.

Typical dimensions for the tubular elements useful in tampon applicators include a length of about 50 to 80 mm, a diameter of about 8 to 20 mm, and a thickness of about 0.1 to 0.6 mm. Preferably, the diameter of the inner tubular element (i.e., the plunger) is less than the diameter of the outer tubular element (i.e., insertion member) to allow for a telescopic arrangement of the inner tubular element within the outer tubular element as shown in FIG. 1.

Any adhesives or methods of attachment may be used to secure the gripping sheet to the insertion member. Examples of suitable adhesives can be found in U.S. Pat. Nos. 4,718, 898 and 4,857,393, the entire contents of which are hereby incorporated by reference.

Various embodiments of the present invention will be evident to one skilled in the art. Accordingly, the scope of the invention should not be limited to the specifics described above but instead be measured with respect to the appended claims.

What is claimed is:

1. An applicator for delivering an object into a body cavity, said applicator comprising:
   a) a tubular insertion member having a longitudinal axis, an outer surface, an insertion end, and a trailing end opposite the insertion end, said trailing end having an edge; and
   b) a finger gripping member having a leading end, a trailing end, and an intermediate portion therebetween, said gripping member comprising a gripping sheet of material, said gripping sheet having an attachment end and an outer end opposite thereof,
   wherein said attachment end is securely attached to said outer surface of said trailing end such that said gripping sheet is wound to be superposed onto itself to form said gripping member with the outer end exposed on an outer surface of the gripping member and the trailing end of the gripping member disposed toward the trailing end edge of the tubular insertion member.

2. The applicator of claim 1, wherein said gripping sheet comprises a portion having at least first and second longitudinal edges, the second longitudinal edge disposed toward the trailing end edge, said gripping sheet superposing onto itself about said insertion member such that a predetermined portion of said gripping member has increased thickness.

3. The applicator of claim 2, wherein said outer end of said gripping sheet is narrower than said attachment end.

4. The applicator of claim 3, wherein said predetermined portion of said gripping member having increased thickness is in the intermediate portion.

5. The applicator of claim 4, wherein the first and second longitudinal edges are oriented along angles oblique to the longitudinal axis of the tubular insertion member at the trailing end thereof.

6. The applicator of claim 3, wherein said predetermined portion of said gripping member having increased thickness is at the gripping member trailing end.

7. The applicator of claim 6, wherein the second longitudinal edge is oriented perpendicular to the longitudinal axis of the tubular insertion member at the trailing end thereof.

8. The applicator of claim 3, wherein said predetermined portion of said gripping member having increased thickness is at the gripping member leading end.

9. The applicator of claim 8, wherein the first longitudinal edge is oriented perpendicular to the longitudinal axis of the tubular insertion member at the trailing end thereof.

10. The applicator of claim 1, wherein said gripping sheet comprises a plurality of adjacent portions, each portion having an attachment end and an outer end opposite thereof, a first portion forming the leading end of the gripping member, and the second portion forming the trailing end of the gripping member whereby the leading and trailing ends of the gripping member are thicker than the intermediate portion disposed therebetween.

11. The applicator of claim 10, wherein the adjacent portions of the gripping sheet are tapered, each outer end being narrower than each respective attachment end.

12. The applicator of claim 1, wherein said gripping sheet comprises a material selected from the group consisting of woven and nonwoven materials, paperboard, paper, cardboard, and laminated paperboard.

13. The applicator of claim 12, wherein said gripping sheet comprises paperboard.

14. The applicator of claim 1, wherein said gripping sheet comprises a material selected from the group consisting of polymers, plastic, plastic sheets, and foam.

15. The applicator of claim 1, wherein said gripping sheet comprises a roughening agent.

16. The applicator of claim 15, wherein said roughening agent comprises pulverized stone or sand, edge deformations, apertures, scoring, plurality of ribs or raised portions.

17. The applicator of claim 1 further comprising means for attaching said gripping sheet to said insertion member.

18. The applicator of claim 1, wherein said means for attaching said gripping sheet comprises an adhesive.

19. The applicator of claim 1, further comprising a plunger slideable within the trailing end of the tubular insertion member.

20. A fingergrip member for providing a raised area of resistance to movement of a user's manual digit, said fingergrip member having a leading end, a trailing end, and an intermediate portion therebetween, said gripping member comprising a gripping sheet of material, said gripping sheet having an attachment end and an outer end opposite thereof, wherein said gripping sheet is wound to be superposed onto itself to form said gripping member with the outer end exposed on an outer surface of the gripping member.

21. The fingergrip of claim 20, wherein said gripping sheet comprises a portion having at least first and second longitudinal edges, said gripping sheet superposing onto itself such that a predetermined portion of said gripping member has increased thickness.

22. The fingergrip of claim 21, wherein said longitudinal edges form a step surface when said gripping sheet is superposed onto itself.

23. The fingergrip of claim 20, wherein said gripping sheet comprises at least two tapered portions.

24. A method of making an applicator for delivering an object into a body cavity, the method comprising the steps of:
  a) providing an tubular insertion member having an outer surface, an insertion end and a trailing end opposite the insertion end, said trailing end having an edge;
  b) encircling a gripping sheet about said trailing end of said tubular insertion member such that said gripping sheet superposes onto itself about said tubular insertion member to form a gripping member having a leading end, a trailing end, and an intermediate portion therebetween wherein the trailing end of the gripping member is disposed toward the trailing end edge of the tubular insertion member.

25. The method of claim 24, wherein said gripping sheet comprises a tapered portion such that said formed gripping member has increased thickness in a predetermined area.

26. The method of claim 24, wherein said gripping sheet comprises a material selected from the group consisting of woven and nonwoven materials, paperboard, paper, cardboard, and laminated paperboard.

27. The method of claim 24, wherein said gripping sheet has two adjacent portions, each portion having an attachment end and an outer end opposite thereof, a first portion forming the leading end of the gripping member, and a second portion forming the trailing end of the gripping member whereby the leading and trailing ends of the gripping member are thicker than the intermediate portion disposed therebetween.

28. The method of claim 24, further comprising the step of attaching said gripping sheet to said insertion member.

29. The method of claim 24, comprising adhering said gripping sheet to said insertion member.

30. A method of making an applicator for delivering an object into a body cavity, the method comprising the steps of:
  a) wrapping a gripping sheet comprising a tapered portion about a mandrel such that said gripping sheet
    superposes onto itself about said mandrel to form a gripping member having a leading end, a trailing end, an intermediate portion therebetween, and increased thickness in a predetermined area
  b) attaching the gripping member to an outer surface of a tubular insertion member having a trailing end terminating at a trailing end edge
  wherein the trailing end of the gripping member is disposed toward the trailing end edge of the tubular insertion member.

31. The applicator of claim 2, wherein said portion of said gripping sheet has a maximum width that is located distal the outer end.

32. The applicator of claim 2, wherein said first and second longitudinal edges are not parallel.

33. The fingergrip of claim 20, wherein said portion of said gripping sheet has a maximum width that is located distal the outer end.

* * * * *